(12) United States Patent
Dyballa et al.

(10) Patent No.: US 10,100,071 B2
(45) Date of Patent: Oct. 16, 2018

(54) HETEROCYCLIC SELENAMONOPHOSPHITES PROTECTED ON A HYDROXYL GROUP AND PROCESSES FOR PREPARATION THEREOF

(71) Applicant: EVONIK DEGUSSA GMBH, Essen (DE)

(72) Inventors: Katrin Marie Dyballa, Recklinghausen (DE); Robert Franke, Marl (DE); Claudia Weilbeer, Bernburg (DE); Detlef Selent, Rostock (DE); Armin Börner, Rostock (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/370,437

(22) Filed: Dec. 6, 2016

(65) Prior Publication Data

US 2017/0158723 A1    Jun. 8, 2017

(30) Foreign Application Priority Data

Dec. 7, 2015   (EP) .................................... 15198145

(51) Int. Cl.
```
C07F 9/547     (2006.01)
C07C 29/00     (2006.01)
C07C 37/00     (2006.01)
C07F 9/655     (2006.01)
C07C 391/02    (2006.01)
C07F 9/6574    (2006.01)
```

(52) U.S. Cl.
CPC ........ C07F 9/65527 (2013.01); C07C 391/02 (2013.01); C07F 9/65517 (2013.01); C07F 9/65522 (2013.01); C07F 9/65742 (2013.01); C07F 9/65744 (2013.01)

(58) Field of Classification Search
None
See application file for complete search history.

(56) References Cited

U.S. PATENT DOCUMENTS

| | | |
|---|---|---|
| 2015/0336865 A1 | 11/2015 | Dyballa et al. |
| 2015/0336885 A1 | 11/2015 | Dyballa et al. |
| 2015/0336995 A1 | 11/2015 | Dyballa et al. |

FOREIGN PATENT DOCUMENTS

| | | |
|---|---|---|
| EP | 2949646 A1 | 12/2015 |
| WO | 2015181018 A1 | 12/2015 |
| WO | 2016139245 A1 | 9/2016 |

OTHER PUBLICATIONS

Chemical Abstract Registry No. 859821-79-7, indexed in the Registry File on STN CAS Online Aug. 12, 2005.*
International Search Report for EP 15 19 8145 dated May 24, 2016 (8 pages).
Selent, Detlef et al. Diastereoisomeric bisphosphite ligands in the hydroformylation of octenes: rhodium catalysis and HP-NMR investigations. Chemical Communications. 2008. 6203-6205.
Franke, R., Selent, D., and Börner, A. Applied Hydroformylation. American Chemical Society, ACS Publications, Chemical Reviews, 2012. 5675-5732.
Tricas, Hugo, et. al. Bulky monophosphite ligands for ethene hydroformylation, J. of Catalysis, 2012, 198-205.
Paine, Tapan Kanti, et. al. Manganese complexes of mixed O, X, O-donor ligands (X = S or Se): synthesis, characterization and catalytic reactivity. Dalton Trans. 2003, 3136-3144.
Kamer, Paul C. J. et. al. Phosphorus (III) Ligands in Homogeneous Catalysis: Design and Synthesis. John Wiley and Sons, LTD. 2012, 94-131.
Lin, He M., et. al. A novel and efficient synthesis of selenides. Arkivoc, 2012, 146-156.

* cited by examiner

*Primary Examiner* — Po-Chih Chen
(74) *Attorney, Agent, or Firm* — Smith, Gambrell & Russell, LLP

(57) ABSTRACT

Novel heterocyclic selenamonophosphites protected on the hydroxyl group, processes for preparation thereof and the use thereof as ligand.

20 Claims, No Drawings

HETEROCYCLIC SELENAMONOPHOSPHITES PROTECTED ON A HYDROXYL GROUP AND PROCESSES FOR PREPARATION THEREOF

Novel heterocyclic selenamonophosphites protected on the hydroxyl group, processes for preparation thereof and the use thereof as ligand.

T. K. Paine describes a synthesis of 2,2'-selenobis(4,6-di-tert-butylphenol) using selenium dioxide. The preparation of 2,2'-selenobis(4,6-di-tert-butylphenol) is effected here in an acidic medium with addition of concentrated hydrochloric acid. The product is obtained with a yield of 25% (T. K. Paine et al., "Manganese complexes of mixed O, X, O-donor ligands (X=S or Se): synthesis, characterization and catalytic reactivity", Dalton Trans., 2003, 15, 3136-3144). It is particularly disadvantageous here that the yields are very low and therefore in need of improvement.

H. M. Lin et al., "A novel and efficient synthesis of selenides", ARKIVOC, 2012, viii, 146-156, discloses another multi-stage synthetic route using Grignard reagents. A synthetic route to selenobiaryl ethers is disclosed in which bromine must first be added onto the corresponding phenol in order to then react the product with magnesium to give a Grignard reagent. The Grignard reagent can then react with the added selenium before the actual coupling to give the biaryl ether:

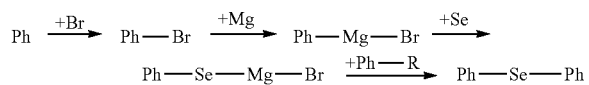

The product was obtained in a good yield, but this synthetic route is very complex, which makes it unattractive for industrial scale use. In this case, a multitude of synthetic steps are needed, the procedure for which is not uncritical in some cases, especially considering scale-up and using standards which are customary in industry. Moreover, this synthetic route gives rise to large amounts of waste products and solvents which have to be disposed of in a costly and inconvenient manner, one reason for which is the use of bromine.

EP 15168645.8 or U.S. Ser. No. 14/720,063 describes a large-scale economic synthetic route for preparing selenodiphenols.

The reactions between olefin compounds, carbon monoxide and hydrogen in the presence of a catalyst to give the aldehydes comprising one additional carbon atom are known as hydroformylation or oxidation. The catalysts used in these reactions are frequently compounds of the transition metals of group VIII of the Periodic Table of the Elements. Known ligands are, for example, compounds from the classes of the phosphines, phosphites and phosphonites, each with trivalent phosphorus $P^{III}$. A good overview of the status of hydroformylation of olefins is found in R. Franke, D. Selent, A. Börner, "Applied Hydroformylation", Chem. Rev., 2012, DOI:10.1021/cr3001803.

Every catalytically active composition has its specific benefits. According to the feedstock and target product, therefore, different catalytically active compositions are used.

Rhodium-monophosphite complexes in catalytically active compositions are suitable for the hydroformylation of branched olefins having internal double bonds. Since the 1970s, there have been descriptions of the use of "bulky phosphites" in hydroformylation (see, inter alia, van Leeuwen et al., Journal of Catalysis, 2013, 298, 198-205). These feature good activity, but the n/i selectivity for terminally oxidized compounds is low and in need of improvement.

In these hydroformylations, monophosphites and bisphosphites are generally used, which are often formed from biphenol units. The development of novel ligands is frequently limited by the available biphenol, that is, ligand units. For instance, 2,2'-selenobiaryl ethers and also diphenylselenoxides and diphenylselenides represent a highly interesting class of compound. The 2,2'-selenobiaryl ethers are currently only being used in certain complexes, especially those containing manganese, but they have great potential for further uses.

The object of the invention was to provide a further wholly novel substance class of ligands in order to broaden the field of available ligands for the respective specific complexes in catalysis. The object also consisted of producing ligands for rhodium hydroformylation catalysts.

The objects are achieved with the heterocyclic selenaphosphites according to claim 1, the process according to claim 7 and the use according to claim 15. Particular embodiments are disclosed in the dependent claims and also detailed in the description. The objects are likewise preferably achieved by selenaphosphites of the structures I and Ia, especially with $R^{1*}$ selected from structures II, IV, V, VI and VII. Particularly preferred compounds here are the hydrogen-, alkyl- and/or —O—$(C_1$-$C_{12})$-alkyl-substituted compounds of the structures II, IV, V, VI and VII of the organofunctional phosphite group —$R^{1*}$, in combination with the —$R^1$ group selected from: —$(C_1$-$C_{12})$— alkyl, —$(C_1$-$C_{12})$-alkyl-O—$(C_1$-$C_{12})$-alkyl, —$(C_6$-$C_{20})$-aryl, —$(C_1$-$C_{12})$-alkyl-O—$(C_6$-$C_{20})$-aryl, —$(C_6$-$C_{20})$-aryl-O—$(C_6$-$C_{20})$-aryl.

The invention provides at least one heterocyclic selenaphosphite compound having a general structure I

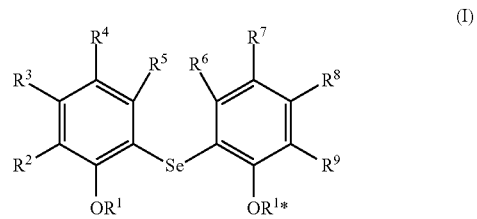

where $R^2$, $R^3$, $R^4$, $R^5$, $R^6$, $R^7$, $R^8$ and $R^9$ may each be independently selected from: —H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen, —OC=O—$(C_1$-$C_{12})$-alkyl, —S-alkyl, —S-aryl, —COO—$(C_1$-$C_{12})$-alkyl, —CONH—$(C_1$-$C_{12})$-alkyl, —CO—$(C_1$-$C_{12})$-alkyl, —CO—$(C_6$-$C_{20})$-aryl, —COOH, —$SO_3H$, —CN,
—N[$(C_1$-$C_{12})$-alkyl]$_2$, where the alkyl groups are linear, branched or cyclic, where the alkyl and aryl groups are each independently unsubstituted or substituted, where each substituted —$(C_1$-$C_{12})$-alkyl group and substituted —$(C_6$-$C_{20})$-aryl group may have at least one substituent and the at least one substituent may in each case independently be selected from
—$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl, and
where the —$R^1$ group may be selected from: —$(C_1$-$C_{12})$-alkyl, —$(C_1$-$C_{12})$-alkyl-O—$(C_1$-$C_{12})$-alkyl, —$(C_6$-$C_{20})$- aryl, —(C₆-C₂₀)-aryl-O—(C₁-C₁₂)alkyl, —(C₁-C₁₂)-alkyl-O—(C₆-C₂₀)-aryl, —(C₆-C₂₀)-aryl-O—(C₆-C₂₀)-aryl —(CO)O—(C₁-C₁₂)-alkyl, acetyl, where the alkyl groups may be linear, branched or cyclic, where the alkyl and aryl groups mentioned may each be independently unsubstituted or substituted, where substituted —(C₁-C₁₂)—alkyl groups and substituted —(C₆-C₂₀)-aryl groups have at least one substituent and the at least one substituent in each case may independently be selected from —(C₃-C₁₂)-cycloalkyl, —(C₃-C₁₂)—heterocycloalkyl, —(C₆-C₂₀)-aryl, fluorine, chlorine, cyano, formyl, acyl or alkoxycarbonyl, and the $R^{1*}$ group is an organofunctional phosphite group.

In accordance with a particularly preferred alternative, the heterocyclic selenaphosphite of the general structure I may have, as —$R^{1*}$, an organofunctional phosphite group selected from the structures II, III, IV, V, VI and VII

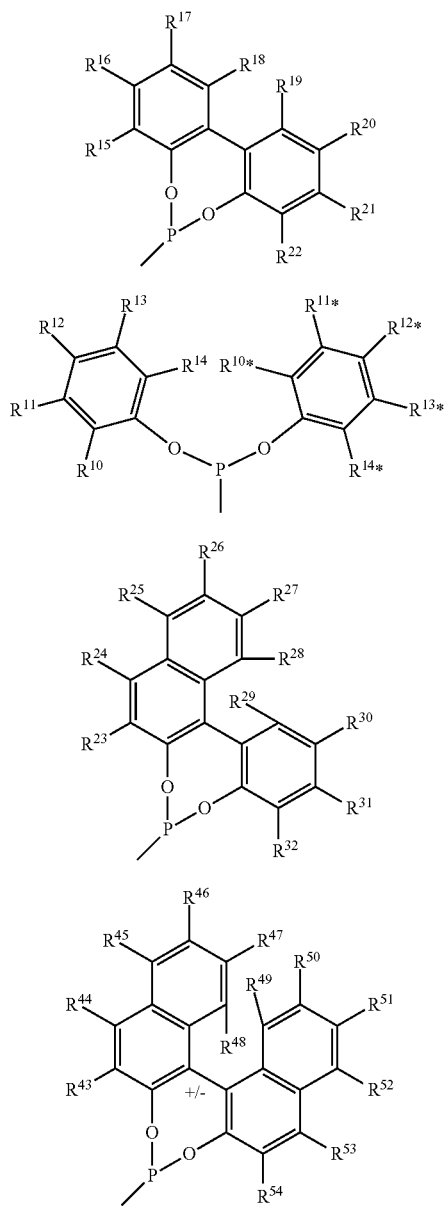

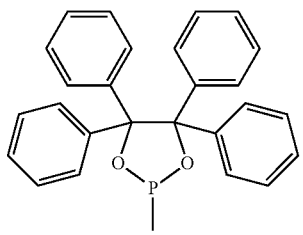

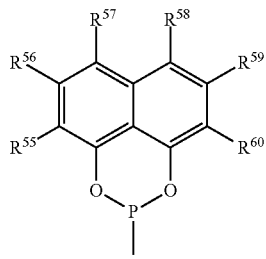

where the radicals $R^{15}$, $R^{16}$, $R^{17}$, $R^{18}$, $R^{19}$, $R^{20}$, $R^{21}$, $R^{22}$ in structure II, $R^{10}$, $R^{11}$, $R^{12}$, $R^{13}$, $R^{14}$, $R^{10*}$, $R^{11*}$, $R^{12*}$, $R^{13*}$, $R^{14*}$ in the structure III, $R^{23}$, $R^{24}$, $R^{25}$, $R^{26}$, $R^{27}$, $R^{28}$, $R^{30}$, $R^{31}$, and $R^{32}$ in structure IV.

$R^{43}$, $R^{44}$, $R^{45}$, $R^{46}$, $R^{47}$, $R^{48}$, $R^{49}$, $R^{50}$, $R^{51}$, $R^{52}$, $R^{53}$ and $R^{54}$ in structure V, $R^{55}$, $R^{56}$, $R^{57}$, $R^{58}$, $R^{59}$ and $R^{60}$ in structure VII.

in each case independently in the respective structure are selected from: —H, —(C₁-C₁₂)-alkyl, —O—(C₁-C₁₂) alkyl, —(C₆-C₂₀)-aryl, —O—(C₆-C₂₀)-aryl, -halogen, where the alkyl groups may be linear, branched or cyclic, where the alkyl and aryl groups may each independently be unsubstituted or substituted, where each substituted —(C₁-C₁₂)-alkyl group and each substituted —(C₆-C₂₀)-aryl group may have at least one substituent and the at least one substituent may in each case independently be selected from —(C₃-C₁₂)-cycloalkyl, —(C₃-C₁₂)-heterocycloalkyl, —(C₆-C₂₀)-aryl, fluorine, chlorine, cyano, formyl, acyl or alkoxycarbonyl.

The invention likewise provides heterocyclic selenaphosphite compounds of the general structure I in which the —$R^1$ group may be selected from:

—(C₁-C₁₂)-alkyl, —(C₁-C₁₂)-alkyl—O(C₁-C₁₂)-alkyl, —(C₆-C₂₀)-aryl, —(C₆-C20)-aryl-O—(C₁-C₁₂)alkyl, —(C₁-C₁₂)-alkyl—O—(C₆-C₂₀)-aryl, —(C₆-C₂₀)-aryl-O—(C₆-C₂₀)- aryl, —(C═O)—O—(C₁-C₁₂)-alkyl, where the alkyl groups may be linear, branched or cyclic, where the alkyl and aryl groups mentioned may each independently be unsubstituted or substituted, where substituted —(C₁-C₁₂)-alkyl groups and substituted —(C₆-C₂₀)-aryl groups may have at least one substituent and the at least one substituent in each case is independently selected from —(C₃-C₁₂)-cycloalkyl and/or —(C₆-C₂₀)-aryl.

In a preferred embodiment, the heterocyclic selenaphosphite of the general structure I may be selected from at least one compound of structure Ia (Ia)

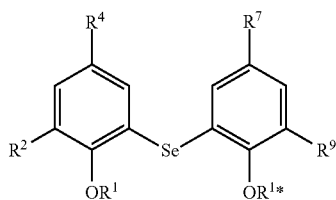

where $R^2$, $R^4$, $R^7$ and $R^9$ may each be independently selected from:
—$(C_1$-$C_{12})$-alkyl, —O—$(C_1$-$C_{12})$-alkyl, —$(C_6$-$C_{20})$-aryl, —O—$(C_6$-$C_{20})$-aryl, -halogen, and where the —$R^1$ group may be selected from —$(C_1$-$C_{12})$-alkyl, —$(C_1$-$C_{12})$-alkyl-O—$(C_1$-$C_{12})$-alkyl, —$(C_6$-$C_{20})$-aryl, —$(C_6$-$C_{20})$-aryl-O—$(C_1$-$C_{12})$-alkyl, —$(C_1$-$C_{12})$-alkyl-O—$(C_6$-$C_{20})$-aryl, —$(C_6$-$C_{20})$-aryl-O—$(C_6$-$C_{20})$-aryl, and the —$R^{1*}$ group in structure Ia may be an organofunctional phosphite group, especially one of the phosphite groups of the structures II, III, IV, V, VI or VII.

In a particularly preferred embodiment, —$R^1$ may in each case independently, in the structures I or Ia, be selected from methoxymethyl-(—$CH_2OCH_3$ (MOM)), —$CH_2OCH_2C_6H_5$ (BOM), —$CH_2OCH_2CH_2OCH_3$ (MEM), benzyl, methyl, tert-butyl, isopentyl.

Likewise preferred compounds include heterocyclic selenaphosphites of the genera structure I or Ia in which —$R^{1*}$ may be selected from the structures II, III, IV, V, VI and VII (II)

(III)

(IV)

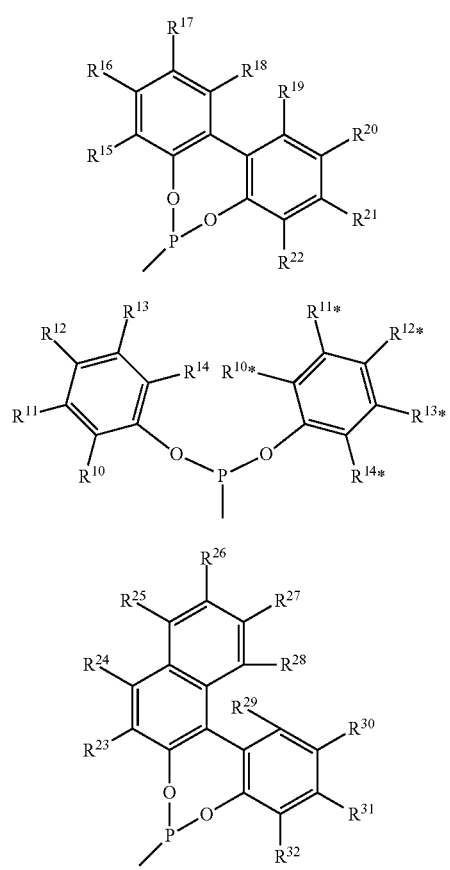

(V)

(VI)

(VII)

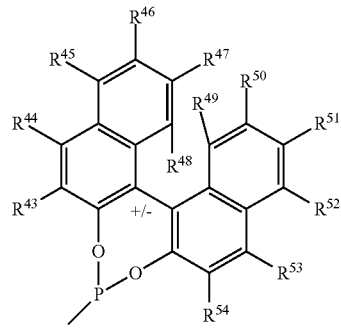

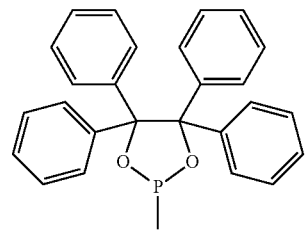

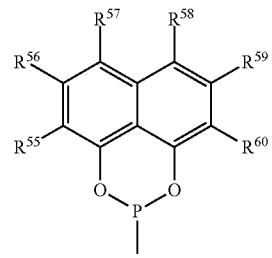

where the radicals
$R^{15}$, $R^{16}$, $R^{17}$, $R^{18}$, $R^{19}$, $R^{20}$, $R^{21}$, $R^{22}$ in structure II,
$R^{10}$, $R^{11}$, $R^{12}$, $R^{13}$, $R^{14}$, $R^{10*}$, $R^{11*}$, $R^{12*}$, $R^{13*}$, $R^{14*}$ in the structure III,
$R^{23}$, $R^{24}$, $R^{25}$, $R^{26}$, $R^{27}$, $R^{28}$, $R^{29}$, $R^{30}$, $R^{31}$ and $R^{32}$ in structure IV,
$R^{43}$, $R^{44}$, $R^{45}$, $R^{46}$, $R^{47}$, $R^{48}$, $R^{49}$, $R^{50}$, $R^{51}$, $R^{52}$, $R^{53}$ and $R^{54}$ in the structure V.
$R^{55}$, $R^{56}$, $R^{57}$, $R^{58}$, $R^{59}$ and $R^{60}$ in structure VII,
in each case for each structure are independently selected from: —H, —$(C_1$-$C_{12})$-alkyl, —$(C_6$-$C_{20})$-aryl, —O—$(C_6$-$C_{20})$-aryl, -halogen, where the alkyl groups are linear, branched or cyclic.

In a further preferred alternative, in the heterocyclic selenaphosphite of the general structure I or Ia, —$R^{1*}$ may be selected from the structure III and the —$R^1$ group may be selected from —$(C_1$-$C_{12})$-alkyl, —$(C_1$-$C_{12})$-alkyl-O—$(C_1$-$C_{12})$-alkyl, —$(C_6$-$C_{20})$-aryl, —$(C_1$-$C_{12})$-alkyl-O—$(C_6$-$C_{20})$-aryl, —$(C_6$-$C_{20})$-aryl-O—$(C_6$-$C_{20})$-aryl, where the alkyl groups are linear, branched or cyclic,

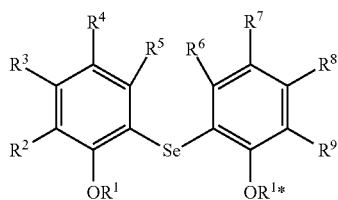

(I)

where $R^2$, $R^3$, $R^4$, $R^5$, $R^6$, $R^7$, $R^8$ and $R^9$ in structure I may each be independently selected from: —H. —($C_1$-$C_{12}$)-alkyl, —O—($C_1$-$C_{12}$)-alkyl, where the alkyl groups are linear, branched or cyclic, or

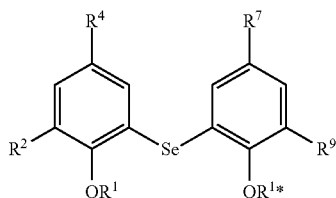

(Ia)

where $R^2$, $R^4$, $R^7$ and $R^9$ in structure Ia may each be independently selected from: —($C_1$-$C_{12}$)-alkyl, —O—($C_1$-$C_{12}$)-alkyl, where the alkyl groups are linear, branched or cyclic, and

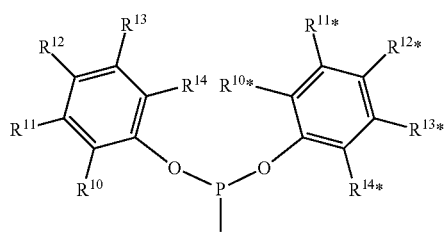

(III)

where $R^{10}$, $R^{11}$, $R^{12}$, $R^{13}$, $R^{14}$, $R^{10*}$, $R^{11*}$, $R^{12*}$, $R^{13*}$, $R^{14*}$ in the structure III may each independently be selected from: —H, —($C_1$-$C_{12}$)-alkyl, —O—($C_1$-$C_{12}$)-alkyl.

In further preferred alternatives, —$R^1$ and —$R^{1*}$ in the heterocyclic selenaphosphite of the general structure I or Ia may be selected from the alternatives with —$R^{1*}$ selected from II, III, IV, V, VI and VII, where the radicals in the structures II, III, IV, V, VI and VII are selected from —H, —($C_1$-$C_{12}$)-alkyl, —O—($C_1$-$C_{12}$)-alkyl and with —$R^1$ selected from methoxymethyl-(—$CH_2OCH_3$ (MOM)), —$CH_2OCH_2C_6H_5$ (BOM), —$CH_2OCH_2CH_2OCH_3$ (MEM), benzyl, methyl, tert-butyl, isopentyl.

In structure Ia, $R^2$, $R^4$, $R^7$ and $R^9$ may each be independently selected from: methyl, ethyl, tert-butyl, isopentyl, methoxy, benzyl, halogen.

In the structure II, $R^{15}$, $R^{16}$, $R^{17}$, $R^{18}$, $R^{19}$, $R^{20}$, $R^{21}$, $R^{22}$ may each independently be selected from: —H, methyl, ethyl, tert-butyl, isopentyl, methoxy, benzyl, halogen.

In the structure III, $R^{10}$, $R^{11}$, $R^{12}$, $R^{13}$, $R^{14}$, $R^{10*}$, $R^{11*}$, $R^{12*}$, $R^{13*}$, $R^{14*}$ may each independently be selected from: —H, methyl, ethyl, tert-butyl, isopentyl, methoxy, benzyl, halogen.

In the structure VIII, $R^{55}$, $R^{56}$, $R^{57}$, $R^{58}$, $R^{59}$ and $R^{60}$ may each independently be selected from: —H, methyl, ethyl, tert-butyl, isopentyl, methoxy, benzyl, halogen.

In structure Ia, $R^2$, $R^4$, $R^7$ and $R^9$ may each be independently selected from: methyl, ethyl, tert-butyl, isopentyl, methoxy, benzyl, halogen, where —$R^1$ may be selected from methoxymethyl (—$CH_2OCH_3$ (MOM)), —$CH_2OCH_2C_6H_5$ (BOM), —$CH_2OCH_2CH_2OCH_3$ (MEM), benzyl, methyl, tert-butyl, isopentyl and —$R^{1*}$ may be selected from structure III where $R^{10}$, $R^{11}$, $R^{12}$, $R^{13}$, $R^{14}$, $R^{10*}$, $R^{11*}$, $R^{12*}$, $R^{13*}$, $R^{14*}$ may each independently be selected from: —H, methyl, ethyl, tert-butyl, isopentyl, methoxy, benzyl, halogen. Preferably, $R^{11}$, $R^{13}$, $R^{14}$, $R^{11*}$, $R^{13*}$, $R^{14*}$ —H and $R^{10}$, $R^{12}$, $R^{10*}$, $R^{12*}$ are selected from methyl, ethyl, tert-butyl, isopentyl.

The invention likewise provides a process for preparing at least one heterocyclic selenaphosphite of the general structure I

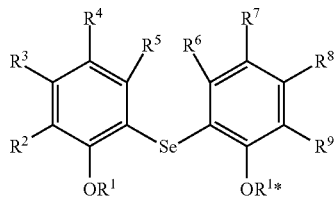

(I)

where $R^2$, $R^3$, $R^4$, $R^5$, $R^6$, $R^7$, $R^8$ and $R^9$ may each be independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —OC=O—($C_1$-$C_{12}$)-alkyl, S-alkyl, S-aryl, —COO—($C_1$-$C_{12}$)alkyl, —CONH—($C_1$-$C_{12}$)-alkyl, —CO—($C_1$-$C_{12}$)-alkyl, —CO—($C_6$-$C_{20}$)-aryl, —COOH, —$SO_3H$, —CN, N[($C_1$-$C_{12}$)-alkyl]$_2$, where the alkyl groups are linear, branched or cyclic, where the alkyl and aryl groups are each independently unsubstituted or substituted, where each substituted —($C_1$-$C_{12}$)-alkyl group and substituted —($C_6$-$C_{20}$)-aryl group may have at least one substituent and the at least one substituent may in each case independently be selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, and where the —$R^1$ group may be selected from: —($C_1$-$C_{12}$)-alkyl, —($C_1$-$C_{12}$)-alkyl-O—($C_1$-$C_{12}$)-alkyl, —($C_6$-$C_{20}$)-aryl, —($C_1$-$C_{12}$)-alkyl-O—($C_6$-$C_{20}$)-aryl, —($C_6$-$C_{20}$)-aryl-O—($C_1$-$C_{12}$)alkyl, —($C_6$-$C_{20}$)-aryl-O—($C_6$-$C_{20}$)-aryl, —(C=O)—O—($C_1$-$C_{12}$)-alkyl, acetyl, where the alkyl group may be linear, branched or cyclic, where the alkyl and aryl groups mentioned may each be independently unsubstituted or substituted, where substituted —($C_1$-$C_{12}$)-alkyl groups and substituted —($C_6$-$C_{20}$)-aryl groups may have at least one substituent and the at least one substituent in each case may independently be selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, and the —$R^{1*}$ group is an organofunctional phosphite group.

comprising at least the process step of (i) reacting a selenodiaryl of the general structure IX

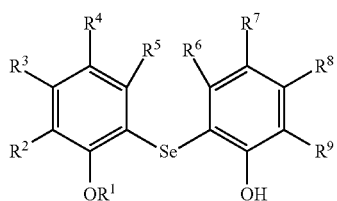
(IX)

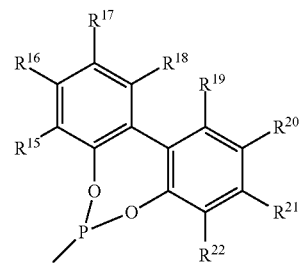
(II)

where $R^2$, $R^3$, $R^4$, $R^5$, $R^6$, $R^7$, $R^8$ and $R^9$ may each be independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —OC=O—($C_1$-$C_{12}$)-alkyl, —S-alkyl, —S-aryl, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —$SO_3H$, —CN, —N[($C_1$-$C_{12}$)-alkyl]$_2$, where the alkyl groups are linear, branched or cyclic, where the alkyl and aryl groups are each independently unsubstituted or substituted, where each substituted —($C_1$-$C_{12}$)-alkyl group and substituted —($C_6$-$C_{20}$)-aryl group may have at least one substituent and the at least one substituent may in each case independently be selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, and —$R^1$ group may be selected from: —$C_1$-$C_{12}$-alkyl, —($C_1$-$C_{12}$)-alkyl-O—($C_1$-$C_{12}$)-alkyl, —($C_6$-$C_{20}$)-aryl, —($C_6$-$C_{20}$)-aryl-O—($C_1$-$C_{12}$)alkyl, —($C_1$-$C_{12}$)-alkyl-O—($C_6$-$C_{20}$)-aryl, —($C_6$-$C_{20}$)-aryl-O—($C_6$-$C_{20}$)-aryl, —(C=O)—O—($C_1$-$C_{12}$)-alkyl, acetyl, where the alkyl group may he linear, branched or cyclic, where the alkyl and aryl groups mentioned may each independently be unsubstituted or substituted, where each substituted —($C_1$-$C_{12}$)-alkyl group and substituted —($C_6$-$C_{20}$)-aryl group may have at least one substituent and the at least one substituent may in each case be independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, (ii) with at least one halophosphite compound $R^{1*}$ Hal of the formula X where Hal is selected from fluorine, chlorine, bromine, iodine, Hal preferably being chlorine, and where —$R^{1*}$ is an organofunctional phosphite group, (iii) and obtaining at least one selenaphosphite of the general structure I, In a preferred embodiment, in the process, the halophosphite compound used is preferably $R^{1*}$ Hal of the formula X with Hal in each case independently selected from fluorine, chlorine, bromine, iodine, Hal preferably being chlorine, and $R^{1*}$ may in each case be selected from the structures II, III, IV, V, VI and VII

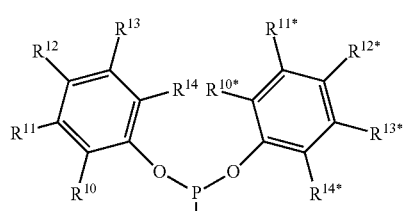
(III)

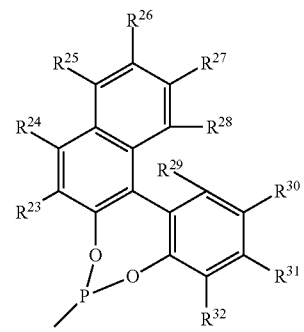
(IV)

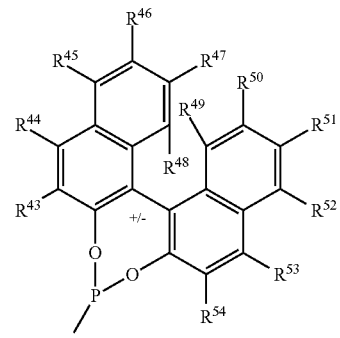
(V)

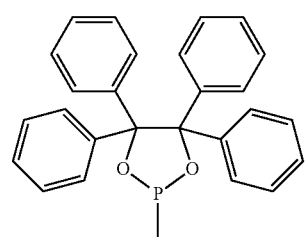
(VI)

(VII)

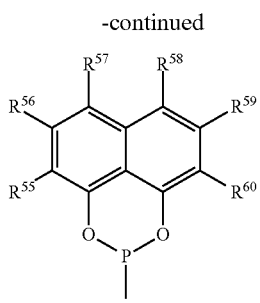

where the radicals
$R^{15}$, $R^{16}$, $R^{17}$, $R^{18}$, $R^{19}$, $R^{20}$, $R^{21}$, $R^{22}$ in structure II,
$R^{10}$, $R^{11}$, $R^{12}$, $R^{13}$, $R^{14}$, $R^{10*}$, $R^{11*}$, $R^{12*}$, $R^{13*}$, $R^{14*}$ in the structure III,
$R^{23}$, $R^{24}$, $R^{25}$, $R^{26}$, $R^{27}$, $R^{28}$, $R^{29}$, $R^{30}$, $R^{31}$, and $R^{32}$ in structure IV,
$R^{43}$, $R^{44}$, $R^{45}$, $R^{46}$, $R^{47}$, $R^{48}$, $R^{49}$, $R^{50}$, $R^{51}$, $R^{52}$, $R^{53}$ and $R^{54}$ in structure V,
$R^{55}$, $R^{56}$, $R^{57}$, $R^{58}$, $R^{59}$ and $R^{60}$ in structure VII.

In each case in each structure are independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, where the alkyl groups may be linear, branched or cyclic:, where the alkyl and aryl groups may each independently he unsubstituted or substituted, where each substituted
—($C_1$-$C_{12}$)-alkyl group and each substituted —($C_6$-$C_{20}$)-aryl group may have at least one substituent and the at least one substituent may each be independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl.

It is further particularly preferred when, in the process, a halophosphite compound $R^{1*}$ Hal of the formula X is used with Hal selected from chlorine, and
—$R^{1*}$ selected from the structures II, III, IV, V, VI and VII
where the $R^{15}$, $R^{16}$, $R^{17}$, $R^{18}$, $R^{19}$, $R^{20}$, $R^{21}$, $R^{22}$ radicals in structure II, $R^{10}$, $R^{11}$, $R^{12}$, $R^{13}$, $R^{14}$, $R^{10*}$, $R^{11*}$, $R^{12*}$, $R^{13*}$, $R^{14*}$ in the structure III, $R^{23}$, $R^{24}$, $R^{25}$, $R^{26}$, $R^{27}$, $R^{28}$, $R^{29}$, $R^{30}$, $R^{31}$ and $R^{32}$ in structure IV, $R^{43}$, $R^{44}$, $R^{45}$, $R^{46}$, $R^{47}$, $R^{48}$, $R^{49}$, $R^{50}$, $R^{51}$, $R^{52}$, $R^{53}$ and $R^{54}$ in structure V, $R^{55}$, $R^{56}$, $R^{57}$, $R^{58}$, $R^{59}$ and $R^{60}$ in structure VII, may each independently be selected from: —H, —($C_1$-$C_{12}$)-alkyl, —O—($C_1$-$C_{12}$)-alkyl, —($C_6$-$C_2$)-aryl, —O—($C_6$-$C_{20}$)-aryl, -halogen, where the alkyl groups are linear, branched or cyclic.

In a particularly preferred process alternative, the selenodiaryl used may be a selenodiaryl of the general structure IXa

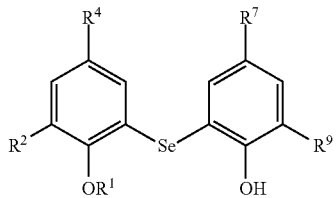

(IXa)

where $R^2$, $R^4$, $R^7$ and $R^9$ may each be independently selected from:
—$C_1$-$C_{12}$)-alkyl, —O—($C_1$-$C_{12}$)-alkyl, —($C_6$-$C_{20}$)-aryl, —O—($C_6$-$C_{20}$)-aryl, -halogen, and where the -$R^1$ group may be selected from: —($C_1$-$C_{12}$)-alkyl, —($C_1$-$C_{12}$)-alkyl-O—($C_1$-$C_{12}$)-alkyl, —($C_6$-$C_{20}$)-aryl, —($C_6$-$C_{20}$)aryl-O—($C_1$-$C_{12}$)alkyl, —($C_1$-$C_{12}$)-alkyl-O—($C_6$-$C_{20}$)-aryl, —($C_6$-$C_{20}$)-aryl-O—($C_6$-$C_{20}$)-aryl, where the alkyl groups may be linear, branched or cyclic.

The conversion of the compound of the structure I can be effected by initially charging the halophosphite compound $R^{1*}$ Hal in a solvent and adding the selenodiaryl of the structure I or Ia, optionally in a mixture with a base, preferably an amine, more preferably an alkylamine, and optionally in a solvent. Alternatively, the reaction can be effected by initially charging the selenodiaryl in a solvent and adding the halophosphite compound, optionally in a solvent.

The invention likewise provides a process in which (i) the reaction is effected in the presence of a base, especially an amine or a pyridine base, preferably an alkylamine such as triethylamine or dimethylaminobutane, more preferably triethylamine.

The invention further provides a process in which the selenodiaryl of the general structure IX or IXa is reacted with $R^{1*}$ Hal of the formula X in a molar ratio of 10:1 to 1:10, preferably in a ratio of 4:1 to 1:4, more preferably in a ratio of 2.5:1 to 1:2.5. Preferably, Hal is chlorine or bromine.

In addition, the (i) reaction is preferably effected at a temperature of −45 to 80° C., particularly of −15 to 30° C., more preferably of −5 to 5° C.

Moreover, (i) the reaction is preferably effected in an aprotic solvent, the solvent especially being selected from organic aromatic halogenated solvents or hydrocarbons.

In a further embodiment, the invention provides for the use of a heterocyclic selenaphosphite of the structure I or Ia as ligand.

The terms "phenol", "aryl" and "phosphite" are used as generic terms in this application and therefore also encompass substituted structures of the compounds mentioned.

The aforementioned definition of substituted —($C_1$-$C_{12}$)-alkyl groups and substituted —($C_6$-$C_{20}$)-aryl groups apply to all groups in which these alkyl or aryl groups are present, i.e. especially also to the following groups: —O—($C_1$-$C_{12}$)-alkyl, —($C_6$-$C_{20}$)-aryl, —O—($C_6$-$C_{20}$)-aryl, —OC=O—($C_1$-$C_{12}$)-alkyl, —(C=O)—O—($C_1$-$C_{12}$)-alkyl.

One or more substituents in the aforementioned structures of the selenaphosphites and selenodiaryls comprise preferably 1 to 10 substituents, in particular 1 to 3.

In the context of the invention, the expression "—($C_1$-$C_{12}$)-alkyl" encompasses straight-chain and branched alkyl groups. Preferably, these groups are unsubstituted straight-chain or branched —($C_1$-$C_8$)-alkyl groups and most preferably —($C_1$-$C_6$)-alkyl groups. Examples of —($C_1$-$C_{12}$)-alkyl groups are particularly methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl,
2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethyipropyl,
1,2,2-trimethylpropyl, 1-ethylbutyl, 1-ethyl-2-methylpropyl, n-heptyl, 2-heptyl,
3-heptyl, 2-ethylpentyl, 1-propylbutyl, n-octyl, 2-ethylhexyl, 2-propylheptyl, nonyl, decyl.

Halogen as substituent on alkyl or aryl includes fluorine, chlorine, bromine and iodine, particular preference being given to chlorine and fluorine.

All elucidations relating to the expression —($C_1$-$C_{12}$)-alkyl in the aforementioned structures of the selenaphosphites and selenodiaryls according to the invention also apply to the alkyl groups in —O—($C_1$-$C_{12}$)-alkyl, that is, in —($C_1$-$C_{12}$)-alkoxy.

Preference is given to unsubstituted straight-chain or branched —($C_1$-$C_6$)-alkoxy groups.

Substituted —($C_1$-$C_{12}$)-alkyl groups and substituted —$C_1$-$C_{12}$)-alkoxy groups in the aforementioned structures of the selenaphosphites and selenodiaryls may have one or more substituents, depending on their chain length. The substituents are preferably each independently selected from: —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl. This definition applies to all substituted alkyl or alkoxy groups of the present invention.

All elucidations relating to the expression —($C_6$-$C_{20}$)-aryl in the aforementioned structures of the selenaphosphites and selenodiaryls according to the invention also apply to the aryl groups in —O—($C_6$-$C_{20}$)-aryl.

Preference is given to unsubstituted —O—($C_6$-$C_{20}$)-groups.

In the context of the present invention, the expression "—($C_6$-$C_{20}$)-aryl and —($C_6$-$C_{20}$)-aryl-($C_6$-$C_{20}$)-aryl-" encompasses mono- or polycyclic aromatic hydrocarbyl radicals. These have 6 to 20 ring atoms, more preferably 6 to 14 ring atoms, especially 6 to 10 ring atoms. Aryl is preferably —($C_6$-$C_{10}$)-aryl and —($C_6$-$C_{10}$)-aryl—($C_6$-$C_{10}$)-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

The expression "—($C_3$-$C_{12}$)-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbornyl or adamantyl.

One example of a substituted cycloalkyl would be menthyl.

The expression "—($C_3$-$C_{12}$)-heterocycloalkyl groups", in the context of the present invention, encompasses non aromatic, saturated or partly unsaturated cycloaliphatic groups having 3 to 12, especially 5 to 12, carbon atoms. The —($C_3$-$C_{12}$)-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— or —S(=O)—. Examples of —($C_3$-$C_{12}$)-heterocycloalkyl groups are tetrahydrothiophenyl, tetrahydrofuryl, tetrahydropyranyl and dioxanyl.

The invention is further illustrated in detail below by examples without the invention being limited to the working examples.

GENERAL METHODS

Solvents and Reagents

All reactions with moisture- and/or oxygen-sensitive substances were carded out in baked-out apparatuses under an argon atmosphere. Solvents for extraction and column chromatography were used at the following purities: dichloromethane (99,9%, Walter, Cat. No, BIE 073107033) ethyl acetate (99.5%, Walter, Cat. No. BIE 003917025) and n-hexane (95%, Walter (Baker), Cat. No. 8669), n-heptane (95%, Walter (Baker), Cat. No, 8662). Other solvents for extraction and column chromatography were of technical quality and were used without further purification unless otherwise stated. Dry solvents (abs.) were purified using a Pure Soy MD-7 System and stored under an argon atmosphere. Benzyl bromide was freshly distilled (17 mbar/ 82° C.) prior to use. Deuterated solvents were distilled from the drying agents specified: dichloromethane-$d_2$ (phosphorus pentoxide), toluene-$d_8$ (1. KOH 2. sodium). Chemicals used for the syntheses were supplied by Sigma Aldrich, Alfa Aesar, Acres Organics, Avantor Performance Materials B. V., Merck KGaA and ABCR GmbH & Co. KG. These were used without further purification unless otherwise stated.

Filtration; Filtrations for the removal of resulting solids were carried out using a G4 frit (pore width: 10-16 µm).
Analysis IR spectroscopy: IR spectra were recorded with a Nicolet 6700 FT-IR spectrometer from Thermo Electron. The substances were measured by ATR methods.

$^1$H NMR spectroscopy: $^1$H NMR spectra were recorded with a model AV 300 (300 MHz) and with the model Fourier 300 (300 MHz) from Broker. Chemical shifts are stated in units on the δ-scale. The residual proton signals of the solvent (dichloromethane-$d_2$: δ=5.32 ppm, toluene-$d_8$: δ=7.09; 7.00; 6.98; 2.09 ppm) served as standard.

$^{13}$C NMR spectroscopy: $^{13}$C NMR spectra were recorded with models AV 300 (75 MHz) and Fourier 300 (75 MHz) from Bruker. The signal of the solvent (dichloromethane-$d_2$: δ=54.0 ppm, toluene-$d_8$;

δ=137.9; 129.2; 128.3; 125.5; 20.4 ppm) served as internal standard wherein the chemical shifts were taken from the broadband $^1$H-decoupled spectra.

$^{77}$Se NMR spectroscopy: $^{77}$Se NMR spectra were recorded with an AV 300 (57 MHz) from Bruker. The spectra were measured in broadband $^1$H-decoupled mode. The chemical shifts are reported in ppm.

Mass spectrometry: EI mass spectra were recorded on a Finnigan MAT 95-XP instrument from Thermo Electron and ESI-TOF mass spectra with a model 6210 Time-of-Flight LC/MS from Agilent.
Autoclave Experiments of Rhodium-Catalysed Hydroformylation The hydroformylation was conducted in a 200 ml autoclave equipped with pressure-retaining valve, gas flow meter, sparging stirrer and pressure pipette from Premex Reactor AG, Lengau, Switzerland. The toluene used as solvent was purified using a Pure Solv MD-7 System and stored under argon. The 1-octene or n-octenes substrate (EVONIK Industries AG, octene isomer mixture of 1-octene: 3.3%; cis+trans-2-octene; 48.5%; cis+trans-3-octene: 29.2%; cis+trans-octene-4: 16.4%; structurally isomeric octenes: 2.6%) used as substrate was heated at reflux over sodium for several hours and distilled under argon.

For the experiments, solutions of the catalyst precursor and the ligand were mixed in the autoclave under an argon atmosphere. [(acac)Rh(COD)] (Umicore, acac=acetylacetonate anion; COD=1,5-cyclooctadiene) was used as catalyst precursor. For experiments at a concentration of 100 ppm-m rhodium, 10 ml of a 4.31 mM solution was placed in the autoclave. Subsequently, the mass of ligand corresponding to a ratio L/Rh=5:1 (or 1:1) was dissolved and mixed in 10 ml of toluene. By adding further toluene, the starting volume of the catalyst solution was adjusted to 41.0 ml. Into a pressure-resistant pipette was filled: 1-octene or n-octanes (10.70 g). The autoclave was heated to the temperatures stated in each case at a total gas pressure (synthesis gas: Linde; $H_2$ (99.999%): CO (99.997%)=1:1) of a) 42 bar for a final pressure of 50 bar or b) 12 bar for a final pressure of 20 bar with stirring (1500 rpm). After reaching the reaction temperature, the synthesis gas pressure was increased to a) 48.5 bar for a final pressure of 50 bar or h) 19.5 bar for a final pressure of 20 bar and the reactant was introduced under a positive pressure of about 3 bar set in the pressure pipette. The reaction was conducted at a constant pressure of 50 or 20 bar (closed-loop pressure controller from Bronkharst, the Netherlands) respectively over 4 h. After the reaction time had elapsed, the autoclave was cooled to room temperature, decompressed while stirring and purged with argon. 1.0 ml of each reaction mixture was removed immediately after the stirrer had been switched off, diluted with 5.0 ml of pentane and analysed by gas chromatography: HP 5890 Series II plus, PONA, 50 m×0.2 mm×0.5 μm.

Some abbreviations: Bn=benzyl; calc.=calculated; MOM=methylmethoxy;

Synthesis of the Precursors

General Procedure—Diphenol Selenides 8.2 mmol of the particular phenol are dissolved in the appropriate solvent (8.2 m). The reaction mixture is heated, and 4.9 mmol of selenium dioxide are added while stirring. The solvent is distilled under reduced pressure (temperature <70° C.), A frit is prepared with 2.5 cm of silica gel (at the bottom) and 2.5 cm of zeolite (at the top). The distillation residue is taken up in the eluent and applied to the filtration column. Cyclohexane:ethyl acetate (95:5) is used to wash the product off the frit and collect it in fractions. The fractions containing the product are combined and freed of the eluent by distillation. The fractions obtained are recrystallized from 95:5 cyclohexane:ethyl acetate. For this purpose, the solid residue is dissolved at 50° C., and insoluble residues are filtered off using a glass frit. The reaction product crystallizes out of the saturated solution at room temperature overnight. The resulting crystals are washed once again with cold cyclohexane.

The structural formula shows the main product obtained in each reaction.

Bis(3,5-dimethyl-2-hydroxyphenyl)selenium: 1a

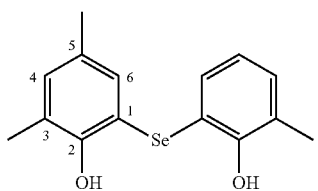

The reaction is conducted according to the general procedure in a screw-top test tube. For this purpose, 1.00 g (8.2 mmol, 1.0 equiv.) of 2,4-dimethylphenol and 0.54 g (4.9 mmol, 0.6 equiv.) of selenium dioxide are dissolved in 1 ml of pyridine and heated. The product is obtained as a colourless crystalline solid.

$^1$H-NMR (400 MHz, CDCl$_3$): δ (ppm)=7.12 (s,2H, 6H), 6.91 (s, 2H, 4H), 5.97 (s,2H, OH), 2.23 (s, 6H, 3-CH$_3$) 2.23 (s, 6H, 5-CH$_3$); $^{13}$C-NMR (100 MHz, CDCl$_3$): δ (ppm)=151.7 (C-2),133.2 (C-3), 133.1 (C-5), 130.4 (C-4), 124.2 (C-6), 114.9 (C-1), 20.3 (5-CH$_3$), 16.5 (3-CH$_3$); $^{77}$Se-NMR (76 MHz, CDCl$_3$): δ (ppm)=163.36 ppm.

Synthesis of the Chlorophosphites

The synthesis of the rnonochlorophosphites such as 6-chlorodibenzo[d,f] [1,3,2]dioxaphosphepine is known to a person skilled in the art and is carried out in a known manner. Chlorophosphites can be prepared from the corresponding dihydroxyl compounds by addition of phosphorus trichloride in the presence of a base. For further information see also "Phosphorus(III) Ligands in Homogeneous Catalysis—Design and Synthesis" by Paul C. J. Kamer and Piet W. N. M. van Leeuwen; John Wiley and Sons, 2012; including p. 94 ff. and references cited therein.

Synthesis of bis(2,4-di-tert-butylphenyl)phosphorochloridite X, 2a

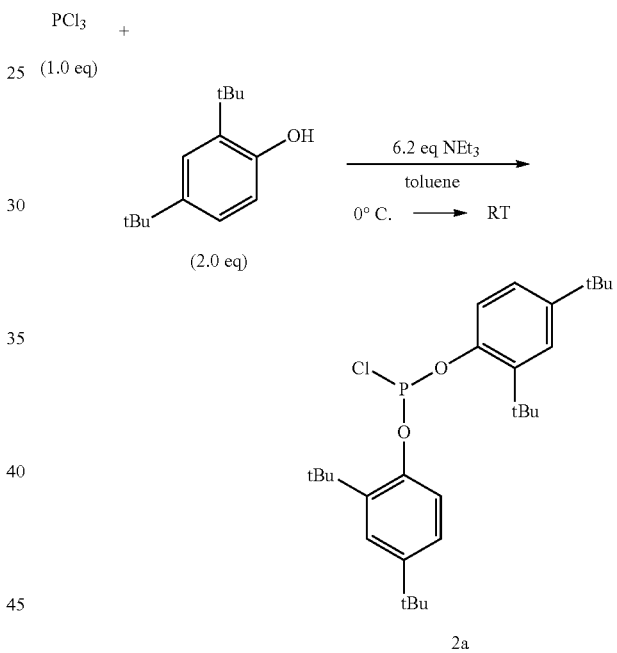

A baked-out 50 ml Schlenk flask under an argon atmosphere was initially charged with 412 mg (2.00 mmol, 2,0 eq) of 2,4-di-tert-butylphenol and 873 μl (638 mg, 6.30 mmol, 6.3 eq) of triethylamine in 10 ml of abs. toluene and cooled to 0° C. Subsequently, 87.5 μl (137 mg, 1.0 mmol, 1.0 eq) of phosphorus trichloride, dissolved in 2.0 ml of abs. toluene, were added dropwise to the cooled solution, in the course of which a colourless precipitate was formed. The latter was rinsed in with 5.0 ml of abs. toluene and the mixture was stirred at RT for 24 h. Subsequently, the reaction mixture was filtered for complete removal of the precipitate formed and the solids were washed with 10 ml of abs. toluene. The solvent was removed under reduced pressure and the crude product was dried under vacuum at 50° C. for three hours. 458 mg (0.962 mmol, 96%, 86% pure) of the title compound 2a were obtained as a colourless solid.

IR (ATR): $\tilde{v}$ (cm$^{-1}$)=2957; 2906; 2869; 1492; 1398; 1362; 1302; 1275; 1247; 1209; 1187; 1157; 1125; 1080; 1020; 941; 907; 887; 863; 819; 776; 745; 699; 645; 579; 532; 490; 464.

$^1$H-NMR (300 MHz, toluene-d8): δ (ppm)=7.54-7.40 (m, 4H, Ar—CH); 7.02 (dd, J=8.5 Hz, J=2.6 Hz, 2H, Ar—CH); 1.50 (s, 18H, —C(CH$_3$)$_3$); 1.24 (d, J=0.9 Hz, 18H, —C(CH$_3$)$_3$);

$^{13}$C-NMR (75 MHz, toluene-d$_8$): δ (ppm)=149.4; 147.1; 139.8 (d, J=2.9 Hz); 124.8, 124.3; 119.9 (d, J=16.2 Hz), 35.16; 34.61; 31.50; 30.41; $^3$P-NMR (122 MHz, toluene-d$_8$): δ (ppm)=161.6 ppm;

MS (El): m/z (%)=476 (16.1) [C$_{28}$H$_{42}$ClO$_2$P]; 461 (100) [C$_{27}$H$_{39}$ClO$_2$P]; 441 (1.69) [C$_{28}$H$_{42}$O$_2$P];

HR-MS (El): calc. for C$_{28}$H$_{42}$ClO$_2$P: 476.25760, found: 476.26031; calc. for C$_{28}$H$_{42}$$^{37}$ClO$_2$P: 478.25760, found: 478.25834; C$_{28}$H$_{42}$ClO$_2$P (476.26 g/mol).

Synthesis of 6-chlorodibenzo[d,f][1,3,2]dioxaphosphepine X

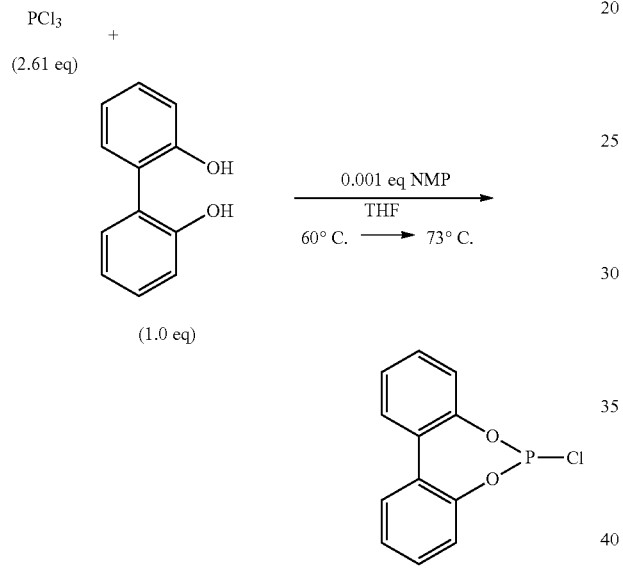

A baked-out 100 ml three-neck flask having a reflux condenser, internal thermometer and dropping funnel was initially charged with 913 μl (1.43 g, 10.4 mmol, 2.61 eq.) of phosphorus trichloride at RT, and 3.80 μl of N-methyl-2-pyrrolidinone were added. The reaction mixture was heated to an internal temperature of 60° C. In a separate 10 ml Schlenk vessel, 745 mg (4.00 mmol, 1.0 eq.) of 2,2-biphenol were dissolved in 20 ml of abs. THF and added to the boiling reaction solution within 15 minutes. The latter was rinsed in with 2.0 ml of abs. THF and the mixture was heated to an internal temperature of 73° C. After a reaction time of 90 minutes, the light brown solution was cooled down to RT and the solvent was removed under reduced pressure. The brown liquid was admixed with 10 ml of abs. THF and the precipitate formed was removed by filtering. The solvent was removed again under reduced pressure and the crude product was dried under vacuum at 50° C. for three hours. 962 mg (3.85 mmol, 96%, 99% pure) of the title compound X were obtained as a dark brown liquid.

IR (ATR): ṽ (cm$^{-1}$)=3064; 3027; 2924; 2848; 2435; 1919; 1601; 1565; 1498; 1474; 1432; 1295; 1273; 1244; 1194; 1172; 1116; 1094; 1042; 1010; 942; 904; 855; 760; 738; 708; 614; 597; 579; 530; 514; 486; 470; 451; 428; $^1$H-NMR (300 MHz, toluene-d8): δ (ppm)=7.29-6.83 (m, 8H, Ar—CH);

$^{13}$C-NMR (75 MHz, toluene-d$_8$): δ (ppm)=149.3 (d, J=5.7 Hz); 137.1; 130.9 (d, J=3.5 Hz); 130.0 (d, J=1.6 Hz); 129.3; 126.0 (d, J=1.2 Hz); 122.0 (d, J=2.2 Hz); $^{31}$P-NMR (122 MHz, toluene-d$_8$): δ (ppm)=180.5; C$_{12}$H$_8$ClO$_2$P (250.00 g/mol).

According to the above experimental methods, it is possible to prepare the following monochlorophosphites of the structure X according to Table 1:

TABLE 1

Monochlorophosphites X

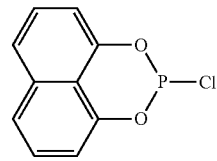

Chloronaphtho[1,8-de][1,3,2]dioxaphosphinine

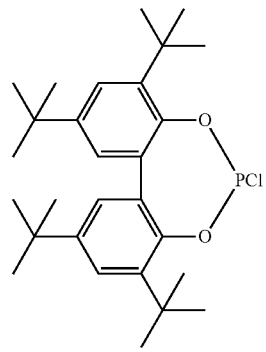

2,2'-Bis(3,5-di-tert-butyl)phenolchlorophosphite

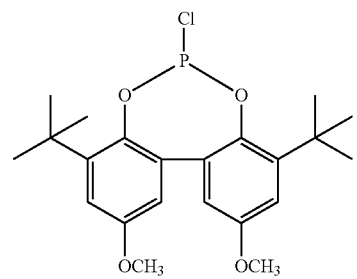

4,8-Di-tert-butyl-6-chloro-2,10-dimethoxydibenzo[d,f][1,3,2]dioxaphosphepine

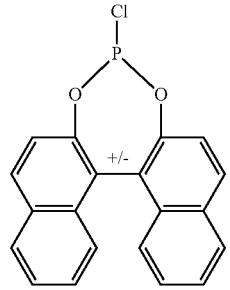

rac-4-Chlorodinaphtho[2,1-d:1',2'-f][1,3,2]dioxaphosphepine

TABLE 1-continued

Monochlorophosphites X

4-Chloro-S-dinaphtho[2,1-d:1',2'-f][1,3,2]dioxaphosphepine

2-Chloro-4,4,5,5-tetraphenyl-1,3,2-dioxaphospholane

Synthesis of 2-((2-(benzyloxy)-3,5-dimethylphenyl)sefanyl)-4,6-dimethylphenol IXA, 3a

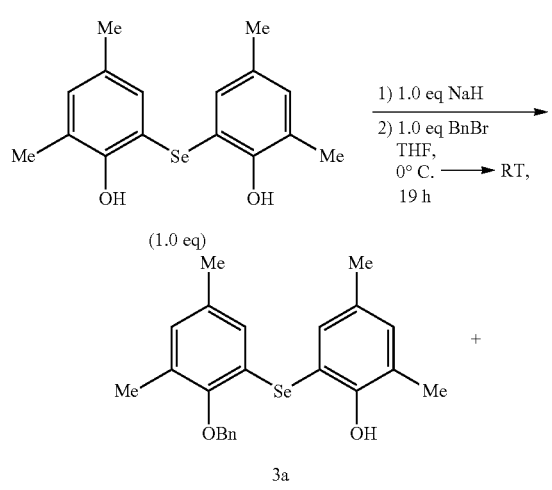

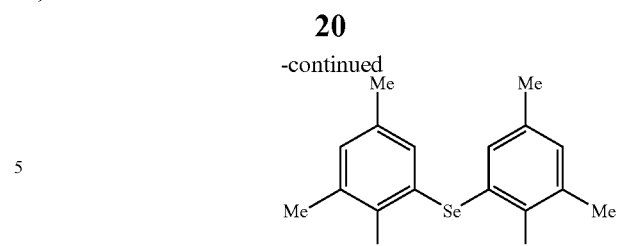

3b

In a baked-out 25 ml Schlenk flask under an argon atmosphere, 40.2 mg (1.01 mmol, 1.0 eq, 60% in paraffin oil) of sodium hydride were suspended in 3.0 ml of abs. THF and cooled to 0° C. Subsequently, 324 rug (1.01 mmol, 1.0 eq) of selenodiphenol, dissolved in 2.0 ml of abs. THF, were added dropwise. The yellowish solution was stirred at 0° C. for 15 minutes and at RT for two hours. Subsequently, at 0° C., 119 µl (172 mg, 1.01 mmol, 1.0 eq) of benzyl bromide were added and the mixture was stirred at 0° C. for 30 minutes. After a further 16 hours at RT, the solvent was removed under reduced pressure. 391 mg of the reaction mixture of 2-((2-(benzyloxy)-3,5-dimethylphenyl)selanyl)-4,6-dimethylphenol 3a (314 mg, 0.762 mmol, 76%) and bis(2-(benzyloxy)-3,5-dimethylphenyl)selane 3b (Bn: benzyl) (76.6 mg, 0.152 mmol, 15%) in a ratio of 4.96:1 (determined from crude $^1$H NMR spectrum) were obtained. It was not possible to separate the reaction mixture completely by column chromatography purification (100% H→100:1→50:1→20:1→10:1 H/DCM). 51.0 mg of 3a were prepared in pure form (analytical evaluation below).

IR (ATR): $\hat{\nu}$ (cm$^{-1}$)=3409; 3030; 3011; 2919; 2854; 2730; 1567; 1497; 1467; 1372; 1328; 1284; 1268; 1251; 1231; 1208; 1123; 1078; 1010; 976; 912; 858; 814; 763; 749; 725; 695; 602; 570; 516; 491; 461; $^1$H-NMR (300 MHz, toluene-d$_8$): δ (ppm)=7.62-7.43 (m, 2H, Ar—CH); 7.36-7.29 (m, 1H, Ar—CH); 7.28-7.08 (m, 2H, Ar—CH); 6.86-6.66 (m, 3H, Ar—CH); 6.58 (d, J=2.1 Hz, 1H, Ar—CH); 4.82 (s, 2H, —OCH$_2$Ph); 2,27 (s, 3H, —CH$_3$); 2.12 (d, J=2.4 Hz. 3H, —CH$_3$); 2.07 (s, 3H, —CH$_3$); 1.86 (s, 3H, —CH$_3$); $^{13}$C-NMR (75 MHz, toluene-d$_8$): δ (ppm) 154.2; 153.2; 137.7; 136.0; 135.1; 134.6; 131.3; 131.2; 129.7; 129.0; 128.6; 128.3; 128.2; 128,1; 74.94; 30.30; 20.53; 20.18; 16.93; 16.31;

$^{77}$Se-NMR (57 MHz, toluene-d$_8$): δ (ppm)=207.3; HR-MS (ESI-TOF): calc. for C$_{23}$H$_{25}$O$_2$Se ([M+H]$^+$): 413.10155, found: 413.10109; calc. for C$_{23}$H$_{24}$O$_2$SeNa ([M+Na]$^+$): 435.0835, found: 435.08378; C$_{23}$H$_{24}$O$_2$Se (412.09 g/mol).

In an analogous manner, 3,3',5,5'-tetra-tert-butylbiphenyl-2,2'-diol, 1c, and bis(3-tert-butyl-5-methyl-2-hydroxyphenyl)selenium, 1b, were reacted with benzyl bromide to give the hydroxyl-protected structures IX, IXa.

Preparation of the Hydroxyl-Protected Monophosphites

Synthesis of 2-((2-(benzyloxy)-3,5-dimethylphenyl)sefanyl)-4,6-dimethylphenyl-bis(2,4-di-tert-butylphenyl)phosphite 1a, 4

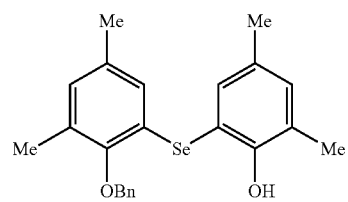

3a

+

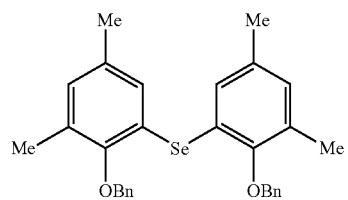

3b (4.96:1 Mono/Dl)
(1.0 eq Mono)

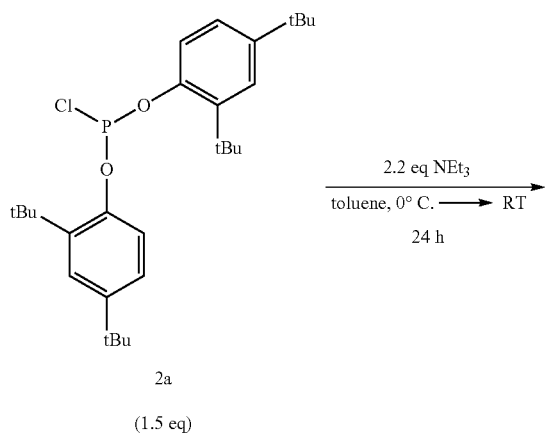

2a
(1.5 eq)

2.2 eq NEt₃
toluene, 0° C. ⟶ RT
24 h

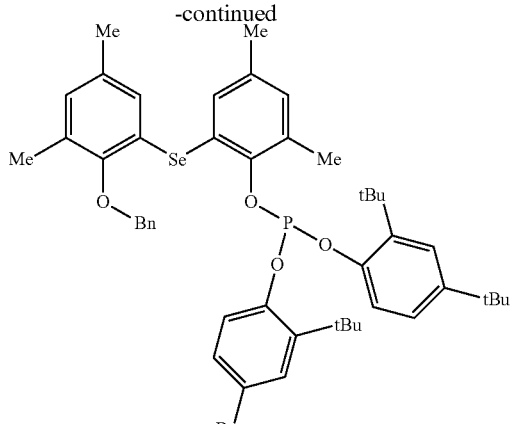

4

In a baked-out 50 ml Schlenk flask under an argon atmosphere, 547 mg (1.15 mmol, 1.5 eq, 86% pure) of dichloro(2,4-di-tert-butylphenyl)phosphorochloridite 2a were dissolved in 10 ml of abs. toluene and cooled to 0° C. In a separate 10 ml Schlenk vessel, 314 mg (0.762 mmol, 1.0 eq, mixture with compound bis(2-(benzyloxy)-3,5-dimethylphenyl)selane 3b, 3a/3b ratio 4.96:1) of 2-((2-(benzyloxy)-3,5-dimethylphenyl)selanyl)-4,6-dimethylphenol 3 and 230 μl (170 mg, 1.68 mmol, 2.2 eq) of triethylamine were dissolved in 10 ml of abs. toluene and added dropwise to the initially charged phosphorochloridite 2a. In the course of this, a yellow colour of the solution was observed with simultaneous formation of precipitate. Subsequently, a further 5.0 ml of abs. toluene were added and the mixture was stirred at 0° C. for 30 minutes and at RT for 16 hours. The reaction mixture was filtered for complete removal of the precipitate formed and the solids were washed with 10 ml of abs. toluene. The solvent was removed under reduced pressure and the crude product was purified by column chromatography (100% H→100:1→50:1→20:1 H/DCM→100% DCM). After the product had been dried under reduced pressure at 50° C. for three hours, 296 mg (0.347 mmol, 45%) of the title compound 4 were obtained as a colourless oil.

IR (ATR): $\hat{v}$ (cm⁻¹)=2955; 2922; 2864; 1491; 1462; 1399; 1361; 1271; 1246: 1191; 1157; 1125; 1082; 1015: 924; 906; 886; 843; 816; 770; 748; 726; 687; 748; 726; 687; 663; 644; 600; 573; 494;

$^1$H-NMR (300 MHz, toluene-d$_8$): δ (ppm)=7.45 (d, J=2.5 Hz, 2H, Ar—CH); 7.43-7.38 (m, 1H, Ar—CH); 7.34 (dd, J=8.4 Hz, J=2.1 Hz, 2H, Ar—CH); 7.26 (d, J=2.5 Hz, 1H, Ar—CH); 7.09 (dt, J=2.2 Hz, J=1.1 Hz, 2H, Ar—CH); 7.03-6.95 (m, 2H, Ar—CH); 6,89-6.81 (m, 3H, Ar—CH); 6,72 (dd, J=1.3 Hz, J=0.7 Hz, 1H, Ar—CH): 6.62-6.57 (m, 1H, Ar—CH); 4.63 (s, 2H, —CH₂Ph); 2.20 (d, J 0.9 Hz, 3H, 5-CH₃); 1.92 (d, J=0.7 Hz, 3H, 5-CH₃); 1.77-1.75 (m, 3H, 3-CH₃):1.74 (d, J=0.7 Hz, 3H, 3-CH₃); 1.29 (s, 18H, —C(CH₃)₃), 1.00 (s, 18H, —C(CH₃)₃); $^{77}$Se-NMR (57 MHz, toluene-d$_8$): δ (ppm)=317.3 ppm (d, $J_{Se-P}$=78.6 Hz); $^{31}$P-NMR (122 MHz, toluene-d$_8$): δ (ppm)=137.0 ($J_{P-Se}$=78.8 Hz);

HR-MS (ESI-TOF): calc. for C$_{51}$H$_{68}$O$_4$PSe ([M+H]⁺): 853.38646, found: 853.38638; calc. for C$_{51}$H$_{65}$O$_4$PSeNa ([M+Na]⁺): 876.37140, found: 876.37119; calc. for C$_{51}$H$_{65}$O$_4$PSeK ([M+K]⁺): 891.34232, found: 891.34248; C$_{51}$H$_{65}$O$_4$PSe (852.38 g/mol).

Hydroformylation

Scheme 1: Illustration of the substance tested in the rhodium-catalysed hydroformylation.

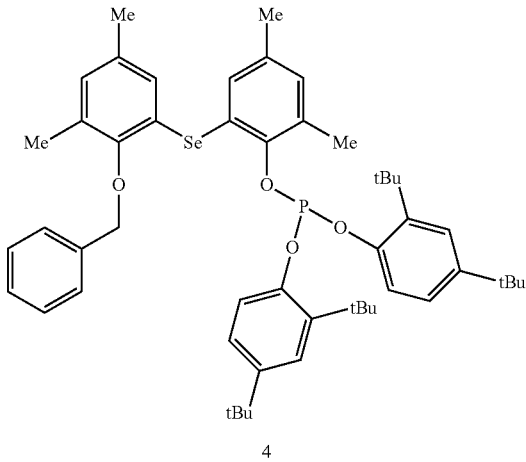

4

TABLE 2

Illustration of the catalysis experiments using organoselenium compounds.

| Entry | Ligand | Olefin/ solvent | Ratio of Rh/ligand/olefin | p [bar] | T [° C.] | t [h] | S [%] |
|---|---|---|---|---|---|---|---|
| 1 | 4* | n-octene/ toluene | 1:5:2230 (100 ppm Rh) | 50 | 120 | 4 | 20.2 |

Elucidations for Table 1:
p = pressure,
T = temperature,
t = time,
Y = yield;
S = n-regioselectivity.
*inventive When the inventive ligand 4 is used, it was possible to achieve good selectivity in the hydroformylation of n-octenes.

Thus, the hydroxyl group-protected selenamonophosphites are usable as ligands in hydroformylation.

The invention claimed is:

1. A heterocyclic selenaphosphite compound having a general structure (I)

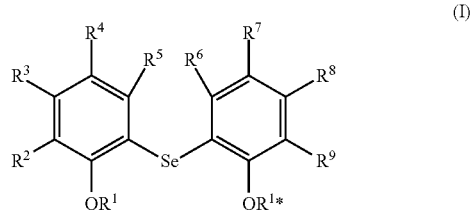

(I)

where $R^2$, $R^3$, $R^4$, $R^5$, $R^6$, $R^7$, $R^8$ and $R^9$ are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —OC=O—($C_1$-$C_{12}$)-alkyl, —S-alkyl, —S-aryl, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —$SO_3H$, —CN, or —N[($C_1$-$C_{12}$)-alkyl]$_2$, where the alkyl groups are linear, branched or cyclic, where the alkyl and aryl groups are each independently unsubstituted or substituted, where each substituted —($C_1$-$C_{12}$)-alkyl group and substituted —($C_6$-$C_{20}$)-aryl group have at least one substituent and the at least one substituent is each independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl, or alkoxycarbonyl, and where the —$R^1$ group is selected from: —($C_1$-$C_{12}$)-alkyl, —($C_1$-$C_{12}$)-alkyl-O—($C_1$-$C_{12}$)-alkyl, —($C_6$-$C_{20}$)-aryl, —($C_1$-$C_{12}$)-alkyl-O—($C_6$-$C_{20}$)-aryl, —($C_6$-$C_{20}$)-aryl-O—($C_1$-$C_{12}$)-alkyl, —($C_6$-$C_{20}$)-aryl-O—($C_6$-$C_{20}$)-aryl, —(C=O)—O—($C_1$-$C_{12}$)-alkyl, -acetyl, where the alkyl groups are linear, branched or cyclic, where the alkyl and aryl groups mentioned are each independently unsubstituted or substituted, where substituted —($C_1$-$C_{12}$)-alkyl groups and substituted —($C_6$-$C_{20}$)-aryl groups have at least one substituent and the at least one substituent in each case is independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl, or alkoxycarbonyl, and the —$R^{1*}$ group is an organofunctional phosphite group.

2. The compound according to claim 1, wherein in the heterocyclic selenaphosphite of the general structure (I) —$R^{1*}$ is an organofunctional phosphite group selected from the structures (II), (III), (IV), (V), (VI) and (VII)

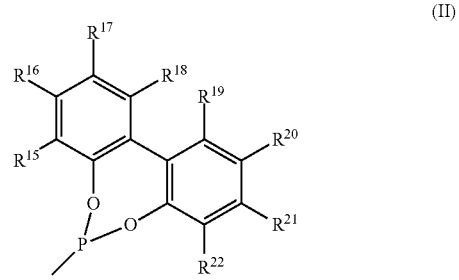

(II)

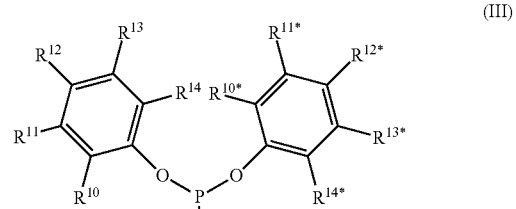

(III)

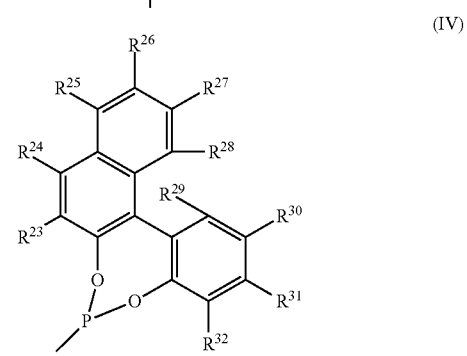

(IV)

-continued

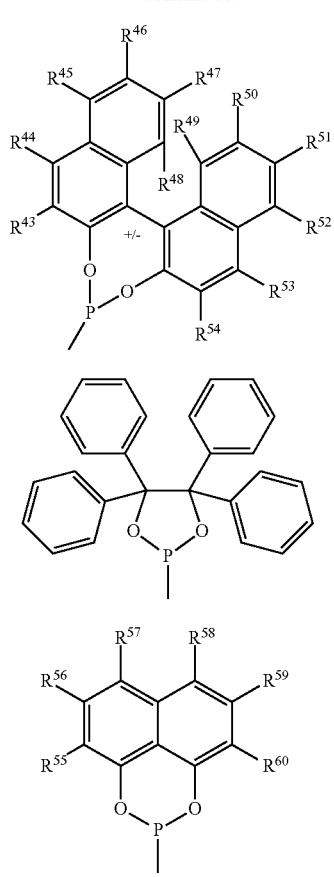

where the radicals
$R^{15}, R^{16}, R^{17}, R^{18}, R^{19}, R^{20}, R^{21}, R^{22}$ in structure (II),
$R^{10}, R^{11}, R^{12}, R^{13}, R^{14}, R^{10*}, R^{11*}, R^{12*}, R^{13*}, R^{14*}$ in the structure (III),
$R^{23}, R^{24}, R^{25}, R^{26}, R^{27}, R^{28}, R^{29}, R^{30}, R^{31}$, and $R^{32}$ in structure (IV),
$R^{43}, R^{44}, R^{45}, R^{46}, R^{47}, R^{48}, R^{49}, R^{50}, R^{51}, R^{52}, R^{53}$ and $R^{54}$ in structure (V), and
$R^{55}, R^{56}, R^{57}, R^{58}, R^{59}$ and $R^{60}$ in structure (VII).
in each case in the respective structure are independently selected from: —H, —$(C_1-C_{12})$-alkyl, —O—$(C_1-C_{12})$-alkyl, —$(C_6-C_{20})$-aryl, —O—$(C_6-C_{20})$-aryl, or -halogen, where the alkyl groups are linear, branched or cyclic, where the alkyl and aryl groups are each independently unsubstituted or substituted, where each substituted —$(C_1-C_{12})$-alkyl group and each substituted —$(C_6-C_{20})$-aryl group has at least one substituent and the at least one substituent in each case is independently selected from —$(C_3C_{12})$-cycloalkyl, —$(C_3-C_{12})$-heterocycloalkyl, —$(C_6-C_{20})$-aryl, fluorine, chlorine, cyano, formyl, acyl or alkoxycarbonyl.

3. The compound according to claim 1, wherein the —$R^1$ group in the structure (I) is selected from: —$(C_1-C_{12})$-alkyl, —$(C_1-C_{12})$-alkyl-O—$(C_1-C_{12})$-alkyl, —$(C_6-C_{20})$-aryl, —$(C_6-C_{20})$-aryl-O—$(C_1-C_{12})$alkyl, —$(C_1-C_{12})$-alkyl-O—$(C_6-C_{20})$-aryl, —$(C_6-C_{20})$-aryl-O—$(C_6-C_{20})$-aryl, —(C=O)—O—$(C_1-C_{12})$-alkyl, where the alkyl groups are linear, branched or cyclic, where the alkyl and aryl groups mentioned are each independently unsubstituted or substituted, where substituted —$(C_1-C_{12})$-alkyl groups and substituted —$(C_6-C_{20})$-aryl groups have at least one substituent and the at least one substituent in each case is independently selected from —$(C_3-C_{12})$-cycloalkyl and/or —$(C_6-C_{20})$-aryl.

4. The compound according to claim 1, wherein the heterocyclic selenaphosphite of the general structure (I) is compound of structure (Ia)

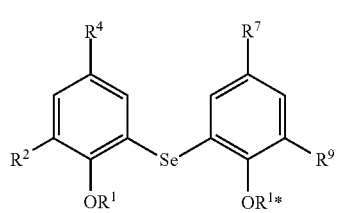

where $R^2, R^4, R^7$ and $R^9$ are each independently selected from:
—$(C_1-C_{12})$-alkyl, —O—$(C_1-C_{12})$-alkyl, —$(C_6-C_{20})$-aryl, —O—$(C_6-C_{20})$-aryl, or -halogen, where the alkyl groups are linear, branched or cyclic,
where the —$R^1$ group is selected from: —$(C_1-C_{12})$-alkyl, —$(C_1-C_{12})$-alkyl-O—$(C_1-C_{12})$-alkyl, —$(C_6-C_{20})$-aryl, —$(C_1-C_{12})$-alkyl-O—$(C_6-C_{20})$-aryl, —$(C_6-C_{20})$-aryl-O—$(C_1-C_{12})$-alkyl, or —$(C_6-C_{20})$-aryl-O—$(C_6-C_{20})$-aryl, where the alkyl groups are linear, branched or cyclic,
and the —$R^{1*}$ group in structure (Ia) is an organofunctional phosphite group.

5. The compound according to claim 4, wherein the —$R^{1*}$ in the heterocyclic selenaphosphite of the structure (Ia) is selected from the structures (II), (III), (IV), (V), (VI) and (VII)

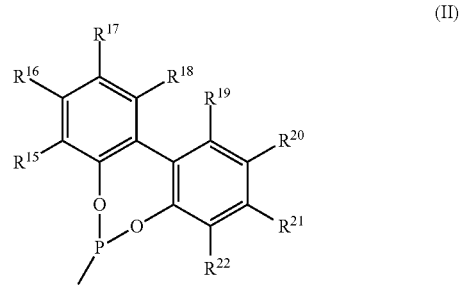

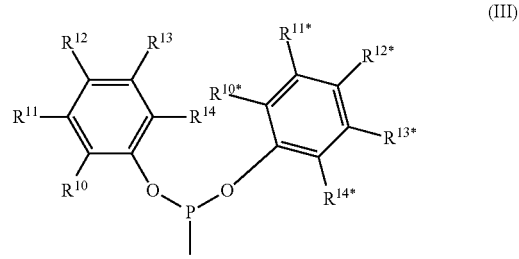

-continued

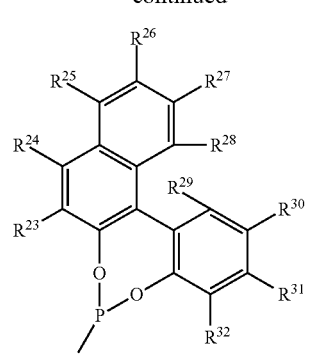

(IV)

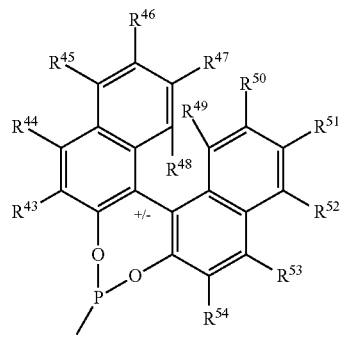

(V)

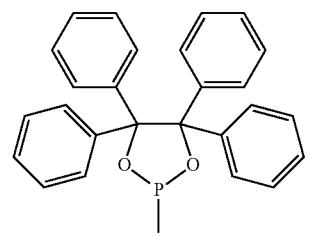

(VI)

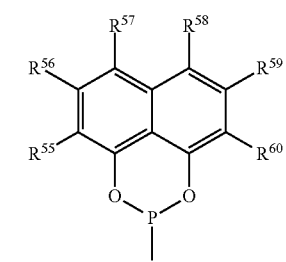

(VII)

where the radicals
$R^{15}, R^{16}, R^{17}, R^{18}, R^{19}, R^{20}, R^{21}, R^{22}$ in structure (II),
$R^{10}, R^{11}, R^{12}, R^{13}, R^{14}, R^{10*}, R^{11*}, R^{12*}, R^{13*}, R^{14*}$ in the structure (III),
$R^{23}, R^{24}, R^{25}, R^{26}, R^{27}, R^{28}, R^{29}, R^{30}, R^{31}$, and $R^{32}$ in structure (IV),
$R^{43}, R^{44}, R^{45}, R^{46}, R^{47}, R^{48}, R^{49}, R^{50}, R^{51}, R^{52}, R^{53}$ and $R^{54}$ in structure (V), and
$R^{55}, R^{56}, R^{57}, R^{58}, R^{59}$ and $R^{60}$ in structure (VII),
in each case for each structure are independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, or -halogen, where the alkyl groups are linear, branched or cyclic.

6. The compound according to claim 4, wherein the —$R^{1*}$ in the heterocyclic selenaphosphite of the structure (Ia) is selected from structure (III)
and the —$R^1$ group is selected from —($C_1$-$C_{12}$)-alkyl, —($C_1$-$C_{12}$)-alkyl-O—($C_1$-$C_{12}$)-alkyl, —($C_6$-$C_{20}$)-aryl, —($C_1$-$C_{12}$)-alkyl-O—($C_6$-$C_{20}$)-aryl, —($C_6$-$C_{20}$)-aryl-O—($C_1$-$C_{12}$)-alkyl, or —($C_6$-$C_{20}$)-aryl-O—($C_6$-$C_{20}$)-aryl, where the alkyl groups are linear, branched or cyclic,

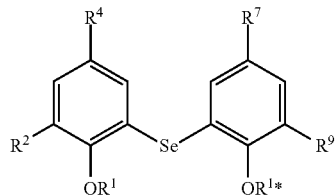

(Ia)

where $R^2$, $R^4$, $R^7$ and $R^9$ in structure (Ia) are each independently selected from —($C_1$-$C_{12}$)-alkyl, or —O—($C_1$-$C_{12}$)-alkyl, where the alkyl groups are linear, branched or cyclic, and

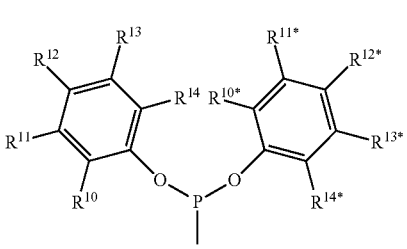

(III)

with $R^{10}, R^{11}, R^{12}, R^{13}, R^{14}, R^{10*}, R^{11*}, R^{12*}, R^{13*}, R^{14*}$ in the structure (III) each independently selected from: —H, —($C_1$-$C_{12}$)-alkyl, —O—($C_1$-$C_{12}$)-alkyl, where the alkyl groups are linear, branched or cyclic.

7. A rhodium hydroformylation catalyst, comprising: the compound according to claim 1 as a ligand.

8. A process for preparing at least one heterocyclic selenephosphite of the general structure (I)

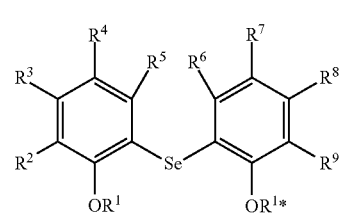

(I)

where $R^2$, $R^3$, $R^4$, $R^5$, $R^6$, $R^7$, $R^8$ and $R^9$ are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —OC=O—($C_1$-$C_{12}$)-alkyl, —S-alkyl, —S-aryl, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —$SO_3$H, —CN, or —N[($C_1$-$C_{12}$)-alkyl]$_2$, where the alkyl groups are linear, branched or cyclic, where the alkyl and aryl groups are each independently unsubstituted or substituted, where each substituted —($C_1$-$C_{12}$)-alkyl group and substituted —($C_6$-$C_{20}$)-aryl group have at least one substituent and the at least one substituent is each independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, and where the —$R^1$ group is selected from: —($C_1$-$C_{12}$)-alkyl, —($C_1$-$C_{12}$)-alkyl-O—($C_1$-$C_{12}$)-alkyl, —($C_6$-$C_{20}$)-aryl, —($C_1$-$C_{12}$)-alkyl-O—($C_6$-$C_{20}$)-aryl, —($C_6$-$C_{20}$)-aryl-O—($C_1$-$C_{12}$)-alkyl, —($C_6$-$C_{20}$)-aryl-O—($C_6$-$C_{20}$)-aryl, —C=O—O—($C_1$-$C_{12}$)-alkyl, or acetyl, where the alkyl groups are linear, branched or cyclic, where the alkyl and aryl groups mentioned are each independently unsubstituted or substituted, where substituted —($C_1$-$C_{12}$)-alkyl groups and substituted —($C_6$-$C_{20}$)-aryl groups have at least one substituent and the at least one substituent in each case is independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, and the —$R^{1*}$ group is an organofunctional phosphite group.

comprising at least the process step of (i) reacting a selenodiaryl of the general structure (IX)

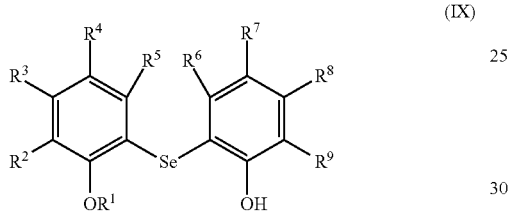

(IX)

where $R^2$, $R^3$, $R^4$, $R^5$, $R^6$, $R^7$, $R^8$ and $R^9$ are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —OC=O—($C_1$-$C_{12}$)-alkyl, —S-alkyl, —S-aryl, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —$SO_3H$, —CN, or —N[($C_1$-$C_{12}$)-alkyl]$_2$, where the alkyl groups are linear, branched or cyclic, where the alkyl and aryl groups are each independently unsubstituted or substituted, where each subtituted —($C_1$-$C_{12}$)-alkyl group and substituted —($C_6$-$C_{20}$)-aryl group have at least one substituent and the at least one substituent is each independently selected from —($C_3$-$C_{12}$)-cycloalkyl, —($C_3$-$C_{12}$)—heterocycloalkyl, —($C_6$-$C_{20}$)-aryl, fluorine, chlorine, cyano, formyl, acyl or alkoxycarbonyl, and —$R^1$ group is selected from: —($C_1$-$C_{12}$)-alkyl, —($C_1$-$C_{12}$)-alkyl-O—($C_1$-$C_{12}$)-alkyl, —($C_6$-$C_{20}$)-aryl, —($C_1$-$C_{12}$)-alkyl-O—($C_6$-$C_{20}$)-aryl, —($C_6$-$C_{20}$)-aryl-O—($C_1$-$C_{12}$)-alkyl, —($C_6$-$C_{20}$)-aryl-O—($C_6$-$C_{20}$)-aryl, —C=O—O—($C_1$-$C_{12}$)-alkyl, or acetyl, where the alkyl groups are linear, branched or cyclic, where the alkyl and aryl groups mentioned are each independently unsubstituted or substituted, where substituted —($C_1$-$C_{12}$)-alkyl groups and substituted —($C_6$-$C_{20}$)-aryl groups have at least one substituent and the at least one substituent in each case is independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, (ii) with at least one halophosphite compound $R^{1*}$Hal where Hal is selected from fluorine, chlorine, bromine, iodine, and where —$R^{1*}$ is an organofunctional bivalent phosphite group, (iii) and obtaining at least one selenaphosphite of the general structure (I).

9. The process according to claim 8, wherein in the halophosphite compounds $R^{1*}$Hal where Hal is in each case independently selected from chlorine, chlorine, bromine, iodine, and —$R^{1*}$ in each case is selected from the structures (II), (III), (IV), (V), (VI) and (VII)

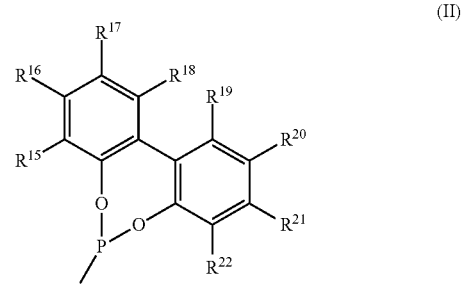

(II)

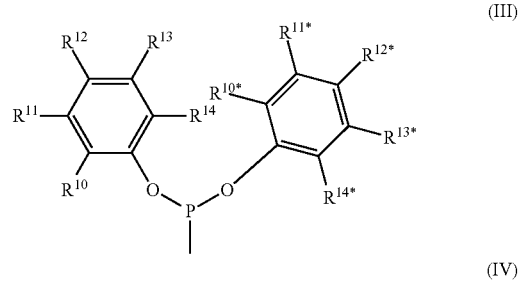

(III)

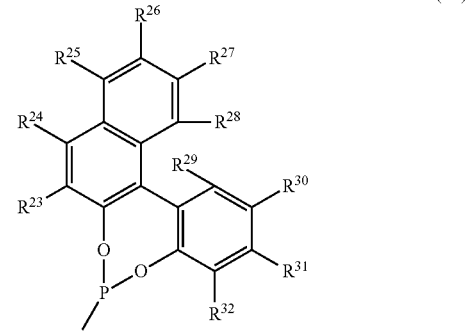

(IV)

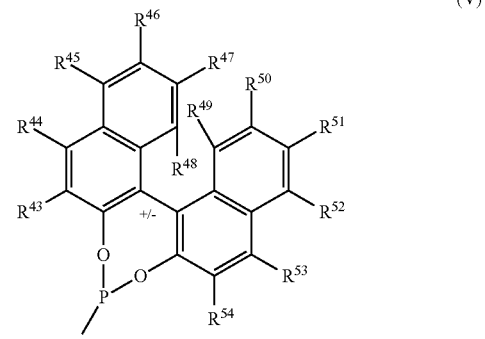

(V)

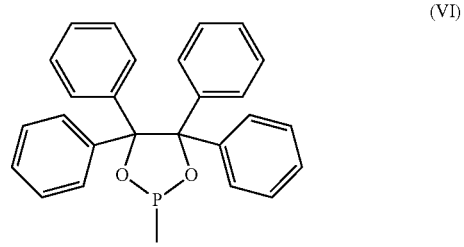

(VI)

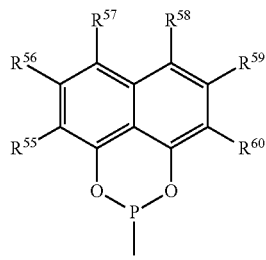 (VII)

where the radicals $R^{15}$, $R^{16}$, $R^{17}$, $R^{18}$, $R^{19}$, $R^{20}$, $R^{21}$, $R^{22}$ in structure (II), $R^{10}$, $R^{11}$, $R^{12}$, $R^{13}$, $R^{14}$, $R^{10*}$, $R^{11*}$, $R^{12*}$, $R^{13*}$, $R^{14*}$ in the structure (III), $R^{23}$, $R^{24}$, $R^{25}$, $R^{26}$, $R^{27}$, $R^{28}$, $R^{29}$, $R^{30}$, $R^{31}$, and $R^{32}$ in structure (IV), $R^{43}$, $R^{44}$, $R^{45}$, $R^{46}$, $R^{47}$, $R^{48}$, $R^{49}$, $R^{50}$, $R^{51}$, $R^{52}$, $R^{53}$ and $R^{54}$ in structure (V), and $R^{55}$, $R^{56}$, $R^{57}$, $R^{58}$, $R^{59}$ and $R^{60}$ in structure (VII), in each case independently in the respective structure are selected from: —H, —$(C_1$-$C_{12})$,-alkyl, —O—$(C_1$-$C_{12})$-alkyl, —$(C_6$-$C_{20})$-aryl, —O—$(C_6$-$C_{20})$-aryl, or -halogen, where the alkyl groups are linear, branched or cyclic, where the alkyl and aryl groups are each independently unsubstituted or substituted, where each substituted —$(C_1$-$C_{12})$-alkyl group and each substituted —$(C_6$-$C_{20})$-aryl group has at least one substituent and the at least one substituent in each case is independently selected from —$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl.

10. The process according to claim 8, wherein in the halophosphite compound $R^{1*}$Hal where Hal is selected from chlorine and bromine, and —$R^{1*}$ is selected from the structures (II), (III), (IV), (V), (VI) and (VII)

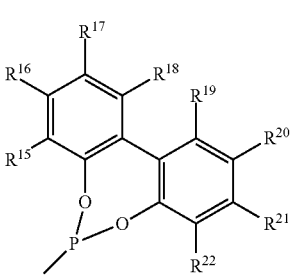 (II)

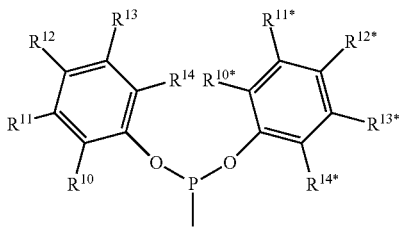 (III)

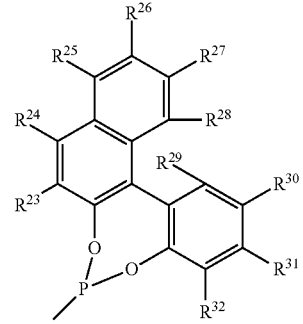 (IV)

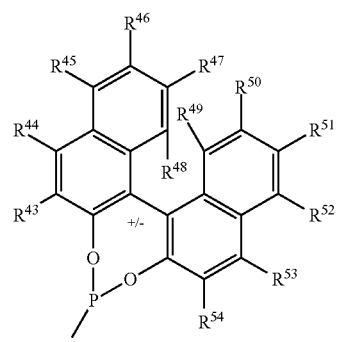 (V)

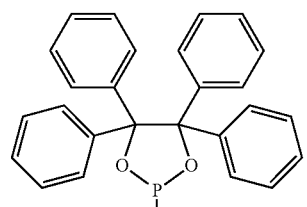 (VI)

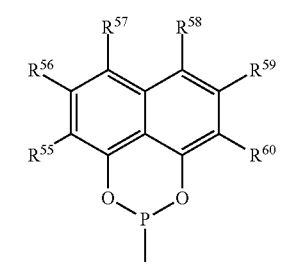 (VII)

where the radicals $R^{15}$, $R^{16}$, $R^{17}$, $R^{18}$, $R^{19}$, $R^{20}$, $R^{21}$, $R^{22}$ in structure (II), $R^{10}$, $R^{11}$, $R^{12}$, $R^{13}$, $R^{14}$, $R^{10*}$, $R^{11*}$, $R^{12*}$, $R^{13*}$, $R^{14*}$ in the structure (III), $R^{23}$, $R^{24}$, $R^{25}$, $R^{26}$, $R^{27}$, $R^{28}$, $R^{29}$, $R^{30}$, $R^{31}$, and $R^{32}$ in structure (IV), $R^{43}$, $R^{44}$, $R^{45}$, $R^{46}$, $R^{47}$, $R^{48}$, $R^{49}$, $R^{50}$, $R^{51}$, $R^{52}$, $R^{53}$ and $R^{54}$ in structure (V), and $R^{55}$, $R^{56}$, $R^{57}$, $R^{58}$, $R^{59}$ and $R^{60}$ in structure (VII), are each independently selected from: —H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen, where the alkyl groups are linear, branched or cyclic.

11. The process according to claim 8, wherein the selenodiaryl corresponds to the general structure (IXa)

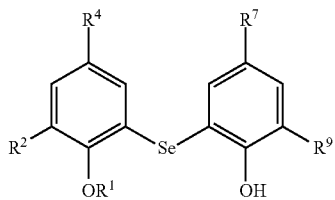
(IXa)

where $R^2$, $R^4$, $R^7$ and $R^9$ are each independently selected from:
—$(C_1$-$C_{12})$-alkyl, —O—$(C_1$-$C_{12})$-alkyl, —$(C_6$-$C_{20})$-aryl, —O—$(C_6$-$C_{20})$-aryl, or -halogen, where the alkyl groups are linear, branched or cyclic, and where the —$R^1$ group is selected from: —$(C_1$-$C_{12})$-alkyl, —$(C_1$-$C_{12})$-alkyl-O—$(C_1$-$C_{12})$-alkyl, —$(C_6$-$C_{20})$-aryl, —$(C_1$-$C_{12})$-alkyl-O—$(C_6$-$C_{20})$-aryl, —$(C_6$-$C_{20})$-aryl-O—$(C_1$-$C_{12})$-alkyl, or —$(C_6$-$C_{20})$-aryl-O—$(C_6$-$C_{20})$-aryl, where the alkyl groups are linear, branched or cyclic.

12. The process according to claim 8,
wherein (i) the reaction is effected in the presence of a base.

13. The process according to claim 11, wherein the selenodiaryl of the structure (IXa) is reacted with $R^1$*Hal in a molar ratio of 10:1 to 1:10.

14. The process according to claim 8,
wherein (i) the reaction is effected in a temperature range from −45 to 80° C.

15. The process according to claim 8,
wherein (i) the reaction is effected in an aprotic solvent.

16. The method of claim 12, wherein (i) the reaction is effected in the presence of an amine base, an alkylamine base, or a pyridine base.

17. The method of claim 16, wherein (i) the reaction is effected in the presence of triethylamine or dimethylaminobutane.

18. The method of claim 13, wherein the selenodiaryl of the structure (IXa) is reacted with $R^1$*Hal in a molar ratio of 4:1 to 1:4.

19. The method of claim14, wherein (i) the reaction is effected in the temperature range from −15 to 30° C.

20. The method of claim 15, wherein (i) the reaction is effected in an aprotic solvent selected from organic aromatic halogenated solvents or hydrocarbons.

* * * * *